(12) United States Patent
Sykes

(10) Patent No.: US 8,646,337 B2
(45) Date of Patent: Feb. 11, 2014

(54) TENSILE TEST DEVICE AND METHOD FOR TESTING DEPOSITS ON ELECTRONIC SUBSTRATES

(75) Inventor: Robert John Sykes, Essex (GB)

(73) Assignee: Nordson Corporation, Westlake, OH (US)

(*) Notice: Subject to any disclaimer, the term of this patent is extended or adjusted under 35 U.S.C. 154(b) by 0 days.

(21) Appl. No.: 13/326,737

(22) Filed: Dec. 15, 2011

(65) Prior Publication Data

US 2012/0204654 A1 Aug. 16, 2012

Related U.S. Application Data

(63) Continuation of application No. 12/303,488, filed as application No. PCT/GB2007/002474 on Jul. 3, 2007, now Pat. No. 8,100,021.

(30) Foreign Application Priority Data

Jul. 3, 2006 (GB) .................................. 0613205.4

(51) Int. Cl.
*G01N 3/08* (2006.01)
*G01N 19/04* (2006.01)

(52) U.S. Cl.
USPC .............................. 73/827; 73/833; 73/150 A

(58) Field of Classification Search
USPC .................................. 73/859, 833, 826, 150 A
See application file for complete search history.

(56) References Cited

U.S. PATENT DOCUMENTS

| | | |
|---|---|---|
| 3,170,322 A | 2/1965 | Cavanaugh |
| 3,698,249 A | 10/1972 | Weaver |
| 4,198,870 A | 4/1980 | Barker et al. |
| 4,292,852 A | 10/1981 | Morris |
| 4,662,229 A | 5/1987 | Curtis |

(Continued)

FOREIGN PATENT DOCUMENTS

| | | |
|---|---|---|
| CA | 2372551 A1 | 8/2003 |
| JP | 6332786 U | 3/1988 |

(Continued)

OTHER PUBLICATIONS

European Patent Office, International Search Report and Written Opinion in PCT Application No. PCT/GB2007/002474, Nov. 8, 2007.
Japanese Patent Office, Office Action in JP Application No. 2009-517418, Jan. 30, 2012.

*Primary Examiner* — Lisa Caputo
*Assistant Examiner* — Jonathan Dunlap
(74) *Attorney, Agent, or Firm* — Wood, Herron & Evans, L.L.P.

(57) ABSTRACT

A tensile testing machine has a jaw which includes a unitary 'H' section member having a cross piece and two uprights. The cross piece is mounted to a cantilever beam which is supported on the test machine and has force measuring elements. A pneumatic actuator applies tensile forces to the first ends of the uprights via strands to urge the first ends apart. When first ends of the uprights are urged apart, their oppositely disposed second ends are urged together to grip a sample deposit to be pulled off a substrate in a tensile test. In use, the jaws can be moved at speed, in the order of 500 mm/s to pull the deposit off of the substrate. The force required to pull the deposit off the substrate in this tensile test is measured by the force measuring elements on the beam.

12 Claims, 6 Drawing Sheets

(56) References Cited

U.S. PATENT DOCUMENTS

| | | |
|---|---|---|
| 5,798,467 A | 8/1998 | Hasegawa et al. |
| 6,237,422 B1 | 5/2001 | Sykes |
| 6,301,971 B1 | 10/2001 | Sykes |
| 6,662,666 B2 | 12/2003 | Hasegawa |
| 7,152,489 B2 | 12/2006 | Hasegawa |
| 7,905,152 B2 | 3/2011 | Sykes |
| 8,100,021 B2 * | 1/2012 | Sykes ............................ 73/827 |
| 2010/0116063 A1 | 5/2010 | Sykes |

FOREIGN PATENT DOCUMENTS

| | | |
|---|---|---|
| JP | 8111417 A | 4/1996 |
| JP | 11288986 A | 10/1999 |
| WO | 2005114722 A1 | 12/2005 |
| WO | 2007102013 A1 | 9/2007 |

* cited by examiner

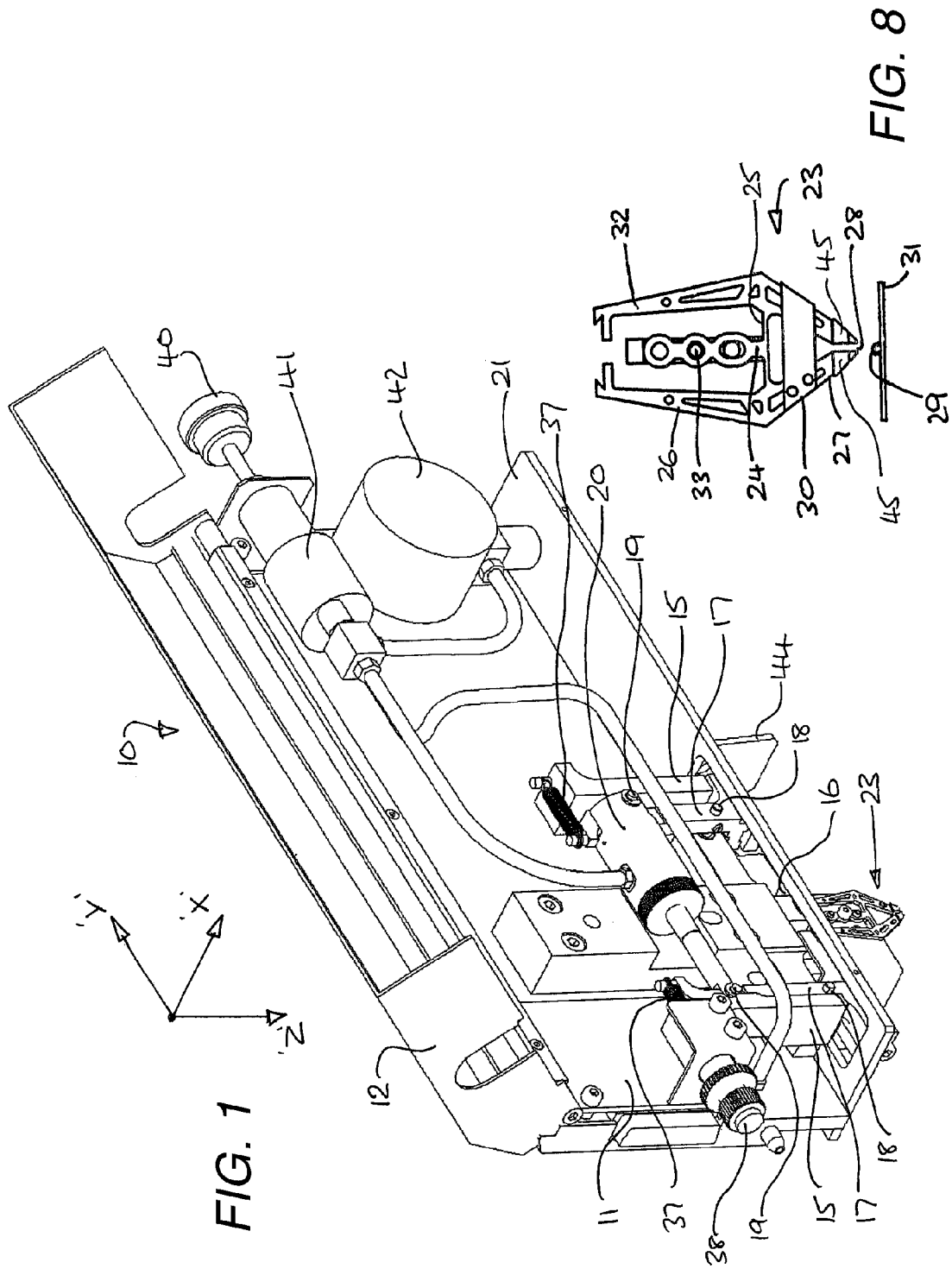

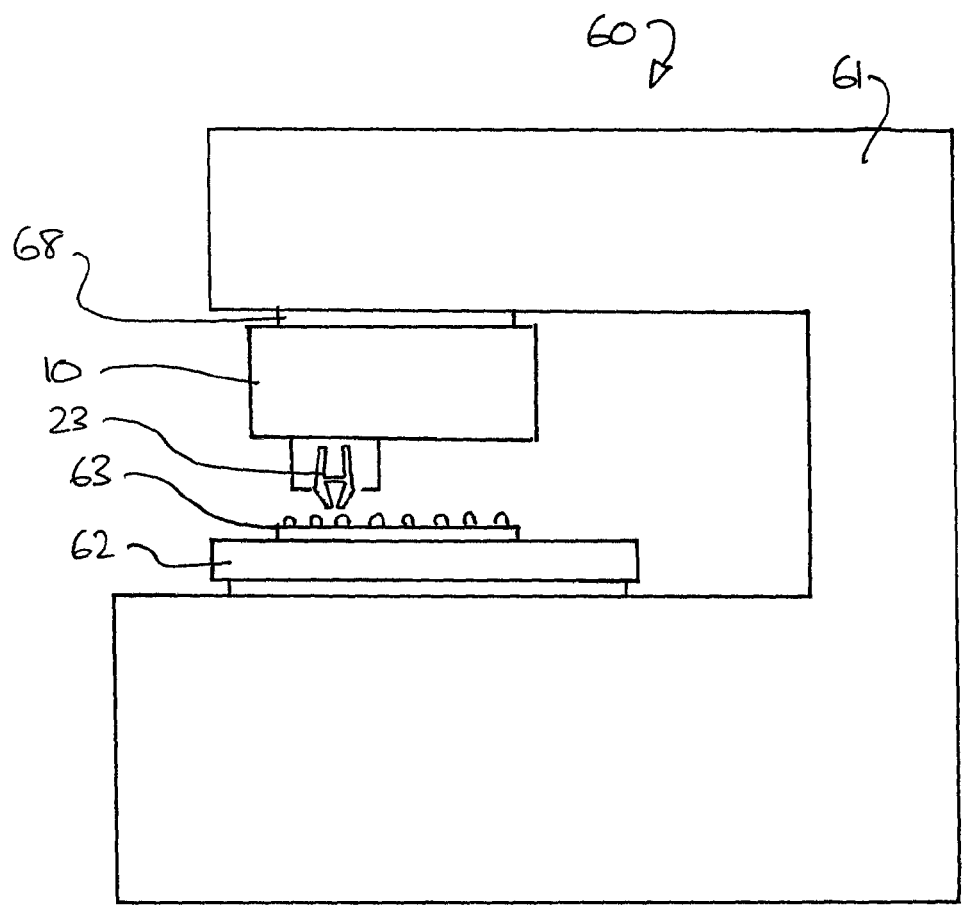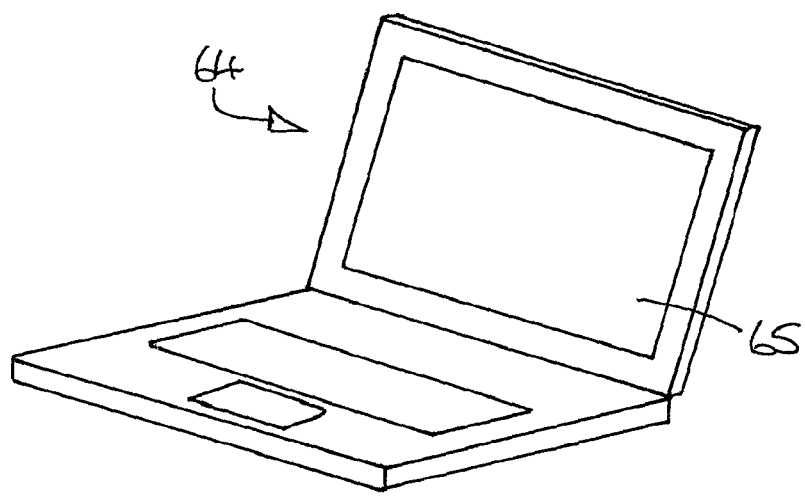
FIG. 9

TENSILE TEST DEVICE AND METHOD FOR TESTING DEPOSITS ON ELECTRONIC SUBSTRATES

BACKGROUND

This invention relates to a device and method of performing a pull test on miniature metallic bonds of electrical equipment.

A substrate for use in electrical apparatus, such as a cell phone, typically defines electrical pathways for connecting electrical components thereof. In miniature devices electrical connections to the substrate are made via soldered or welded connections, and for this purpose metallic balls, for example of solder, are formed on the component and re-flowed or welded when assembled to a mating substrate.

Typically a component may be in the range 5-50 mm and have solder balls thereon. Such components are often termed BGA's (ball grid arrays). These balls have the appearance of a low circular dome or squashed sphere, and have a diameter in the range 0.1-1.0 mm.

It is necessary to test the mechanical strength of the bond between the solder ball and the substrate in order to give confidence that the production bonding method is adequate, and that the bond strength is sufficient. One kind of test applies a tension load to the solder ball by gripping and pulling. In use a strong bond will result in ductile failure of the solder ball, with progressive deformation until the solder ball breaks away; part of the solder ball remains adhered to the substrate. A weak bond will typically exhibit brittle failure and tear away from the substrate leaving little residue adhered thereto.

The very small size of solder balls, and/or the low detected forces have resulted in the development of specialist test equipment. Such equipment may be semi-automated so that successive balls on a component are indexed one by one to a test position, for pull testing.

In particular, devices have been developed with jaws to grip a solder ball so as to exert a pulling (tension) load. The pulling load is applied generally perpendicular to the bonding plane. Very low forces are detected by the use of special low friction techniques.

These very low forces can be successfully and accurately measured, using a force transducer, when the gripping head of the test device is moving slowly. However if high pull testing speeds are required (greater than 15 mm/sec), the inertial mass of the moving part(s) may mask the force required to break the mechanical bond. One aim of the present invention is thus to provide a low mass arrangement capable of exerting high gripping forces at the gripping head, and also capable of high speed testing.

A problem can exist with existing test devices where displacement of the gripping head is via a displacement member (or beam) having the force transducer thereon. If movement of the gripping head from an unclamped to a clamped condition on the sample being tested introduces strain into the displacement member, that strain will be measured by the force transducers and affect the absolute values of tensile stress recorded during testing. For example a slight initial strain on clamping may skew tensile values notwithstanding that the strain gauge output is zeroed prior to commencement of the test. It is desirable to de-couple to the greatest extent, displacement of the gripping head during clamping and force measurement. This is achieved in the apparatus of the present invention as described in more detail below. This feature is advantageous both for low and high speed testing.

Yet another potential difficulty is to maximize the potential testing speed. Stiffness of the gripping head is an important factor because if the chosen testing speed is of the same order as the resonant frequency of the gripping head, the test results will be inaccurate. Therefore, the gripping head should be stiff. However since force measurement conventionally relies upon strain of a beam, i.e. bending, too much stiffness will reduce sensitivity. Accordingly, a compromise which allows a gripping head with high resonant frequency and high stiffness is desirable, resulting in a system which has a suitable bandwidth for the high speed testing, but can also be used for conventional low speed testing.

Typically 'high speed' means greater than 15 mm/s, and as high as 1000 mm/s. Conventional testing, in which a gripper pulls a deposit off a substrate, is typically in the range 0.1-15 mm/s, and is referred to in this specification, comparatively, as 'low speed' testing.

SUMMARY

According to a first aspect, the invention comprises a jaw of a tensile test device, said jaw comprising a unitary substantially 'H' shaped member having a cross piece adapted for mounting to a strain gauged cantilever beam, and two uprights, the upper ends of the uprights being adapted to be urged resiliently apart so as to bring the lower ends of the uprights towards one another to grip a test sample. Once the jaw is gripping the sample, the cantilever beam is moved upward by the test device so that an upward tensile force is transmitted to the cross piece and thence to the test sample via the lower ends of the uprights. The upper ends of the uprights which are being pulled apart to cause the jaw to grip the sample are substantially isolated from this tensile force load path.

Such a jaw can be formed by photo-etching from, for example, stainless steel sheet. The uprights are arranged to bend resiliently about the cross piece in the manner of a living hinge. The cross piece is typically of smaller section than the uprights at least at the ends thereof. The uprights themselves are however relatively stiff so as to be able to grip the test sample without bending, and are of comparatively large section relative to the ends of the cross piece. The uprights may include apertures to reduce the mass thereof, especially by removal of material from low stress areas, for example on the neutral axis thereof.

Preferably the jaw is no more than 10 g in weight, and in one embodiment is less than 5 g in weight.

The said other ends of the uprights may approach so as to define a narrow jaw gap suited to the maximum dimension of the sample to be gripped. The other ends may be shaped to better conform to the shape of the sample.

In the preferred embodiment the jaw is symmetrical.

In a preferred embodiment the jaw of the invention is mounted to the free end of a cantilever beam, the beam axis being substantially orthogonal to the axis of said uprights and to the axis of said cross piece, and said beam comprising a force measuring element.

In a preferred embodiment, said beam incorporates one or more strain gauges to relate deflection thereof to applied force. In this way the pulling force acting on said sample via said jaw is applied via said beam, and can be determined in a substantially friction-free manner. Thus pulling force is independent of the clamping force applied by urging the uprights apart.

In one embodiment the cantilever beam comprises a multi-component device having a main beam element comprising a cantilever spring and a minor beam element connected at its ends to the main beam element, and acting as a force detecting member. The minor beam element is typically strain gauged to allow bending thereof to be related to the force applied to the sample. The main beam element may have a minor beam element on either side thereof. In a preferred embodiment the beam comprises three parallel beam elements having ends connected at one side to said jaw, and at the other side being connectable to a main frame element. Multiple parallel beam elements are desirable in order to ensure that jaw movement is on a single (typically vertical) axis, rather than in an arc.

Preferably the uprights are actuated by respective tension elements directed oppositely. By utilizing tension elements, the mass and stiffness thereof can be low compared with compression elements. Flexible tension elements effectively de-couple the mass of the actuator for the tension elements from the mass of the jaw and cantilever beam by resisting transmission of forces from the actuator to the jaw except for the tensile forces used to actuate the jaw. Thus compressive forces and bending forces cannot be transmitted to the jaw in any substantial amount by the tension elements. The tension elements are very compliant, by which is meant that the compliance is sufficient to resist transmission of other forces.

According to another aspect of the invention there is provided an actuating frame for a jaw of the kind noted above, the frame having two generally parallel limbs symmetrically pivoted therein, the upper ends of the limbs being connected by a pneumatic actuator at one side of the pivots and the lower ends of the limbs being adapted for connection to the uprights of a spring jaw by tension members in the form of strands, wherein in use the actuator pulls the upper ends of the limbs together to cause the lower ends of the limbs to pivot outwardly in order to tension the strands and pull on the uprights of the spring jaw.

Preferably suitable return springs urge said limbs to a rest condition in which tension forces are not applied to the strands. In one embodiment said return springs comprise coiled wire tension springs anchored one each between a limb and said frame.

The actuating frame may further include setting means to determine the rest condition of said limbs. In the preferred embodiment said setting means comprise screw-threaded adjusters anchored in said frame and movable relative thereto to bear on respective limbs. Furthermore said tension members may include an adjustable anchor to permit a pre-load to be applied to said limbs.

According to yet another aspect of the invention, there is provided a method of measuring the tensile force required to pull a deposit off a substrate, and comprising the steps of:

providing a unitary jaw for gripping a deposit, said jaw having open and closed conditions, and a pulling direction, mounting said jaw on the free end of a cantilever beam extending perpendicularly to said direction, said beam having a strain gauge thereon to relate bending thereof to an applied force, providing an actuator for closing said jaw and operable by applying a tension load in a direction mutually perpendicular to the direction of extension of said beam and to said pulling direction, positioning a deposit in said jaw, said jaw being in the open condition, operating said actuator to close said jaw about said deposit, applying an increasing pulling force in said pulling direction via said beam; and recording the electrical output of said strain gauge.

The method may include the preliminary step of driving the jaw relatively to the deposit to position the jaw within the deposit.

In a preferred embodiment, the deposit is first positioned under said jaw at a distance and in a plane perpendicular to said pulling direction, and said jaw is subsequently moved in the open condition relatively towards and over said deposit for subsequent closure on said deposit.

Preferably the deposit is stationary with respect to the machine frame, and the jaw is moved downwardly to grip the deposit.

According to still another aspect of the invention, there is provided a method of measuring the tensile force required to pull a deposit off a substrate, comprising the steps of:

providing a unitary jaw for gripping a deposit, said jaw having open and closed conditions, and a pulling direction, mounting said jaw on the free end of a cantilever beam, said beam having a strain gauge thereon to relate bending thereof to an applied force, providing an actuator for closing said jaw by applying a tension load, positioning a deposit in said jaw, said jaw being in the open condition, operating said actuator to close said jaw about said deposit, moving said jaw and deposit together in said pulling direction at a predetermined speed, abruptly halting said deposit, and recording the electrical output of said strain gauge.

Other features of the invention will be apparent from the following description of a preferred embodiment shown by way of example only in the accompanying drawings in which:

BRIEF DESCRIPTION OF THE DRAWINGS

FIG. 1 is an isometric front view of a test cartridge according to the invention, with cover open;

FIG. 8 is an enlarged front elevation of the jaw of FIG. 1.

FIG. 9 illustrates schematically a testing apparatus.

DETAIL DESCRIPTION

Figure 6:
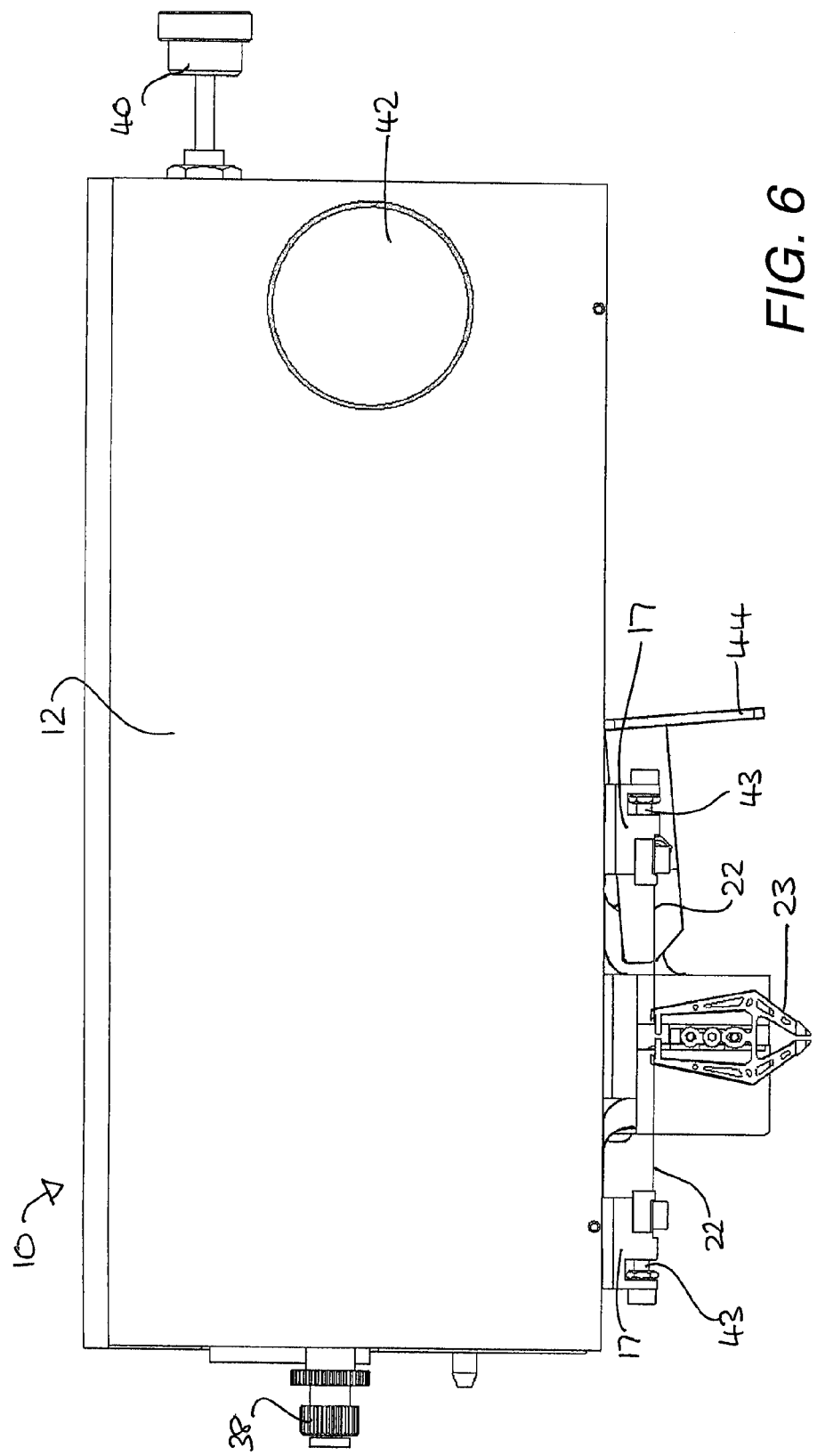
FIG. 6 is a front elevation of the cartridge of FIG. 1, with cover closed.

With reference to FIGS. 1 and 6 a test cartridge 10 is adapted for mounting in a test machine having sufficient axes of movement to move the cartridge in a desired direction with respect to a test piece. The test piece may for example be mounted on a fixed base plate, and the cartridge be movable about X and Y axes to position gripping jaws at a test location, and in the Z axis to allow the jaws to approach and grip a test ball, and to apply a pull test. An example of a prior art test machine is the Series 4000 machine sold by Dage Precision Industries of Aylesbury, England.

Alternatively the test piece may be movable on an X-Y table, and the test cartridge be confined to Z axis movement. Typical X, Y and Z axes are illustrated.

The cartridge 10 comprises a chassis 11 having a hinged cover 12 to conceal and protect sensitive components; the cover is shown in the open condition in FIG. 1.

Mounted on the chassis is a frame having two uprights 15. Inboard of each upright 15 and passing through an aperture 16 in frame 11, are generally upright legs 17. The legs 17 are pivoted with respect to the uprights 15 by pins 18, and are connected at pivot pins 19 by a pneumatic ram 20, situated between the uprights 15.

As an alternative to the pneumatic ram 20, the device could alternatively use other means such as an electric motor or an electro-magnet.

The lower ends of the legs 17 protrude through a lower flange 21 of the chassis 11 and each is coupled to a tension member 22 which acts on a respective arm of a jaw 23 (FIG. 6).

Figure 2:
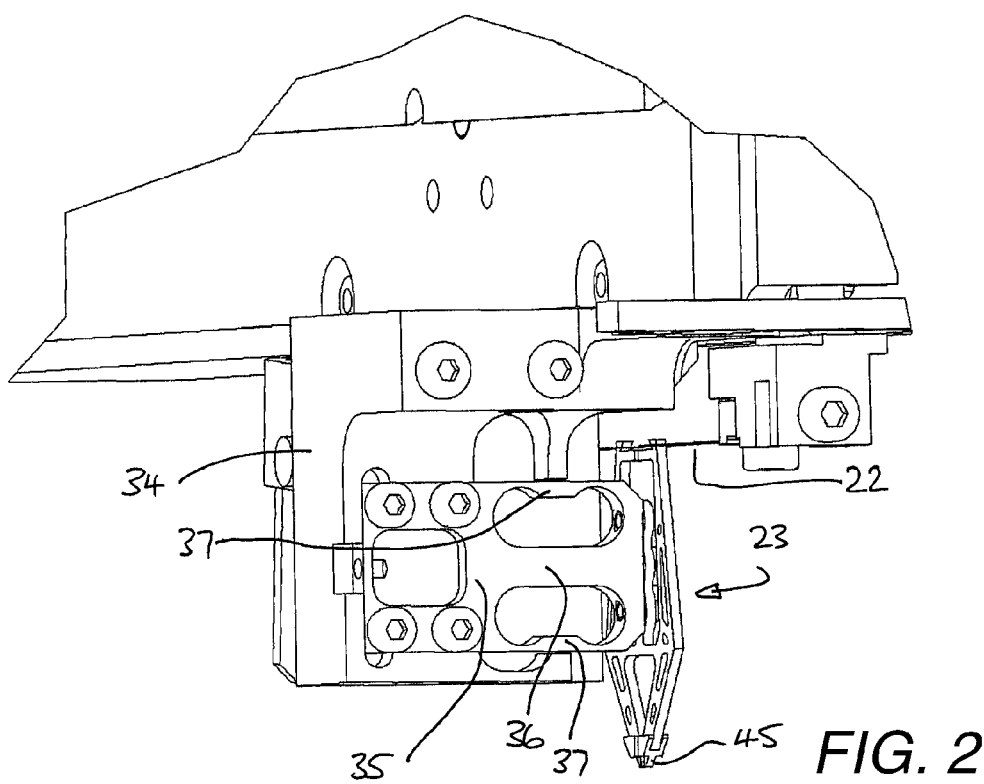
FIG. 2 is an enlarged elevation from one side of the jaw arrangement of FIG. 1.

The jaw 23 is more clearly illustrated in FIGS. 2 and 8 and comprises a unitary generally 'H' shaped symmetrical metal component having a central mounting limb 24 extending from the upper side of the cross piece 25. Each arm 26 is a mirror image, and has a lower portion 27 which approaches the centre-line. These lower portions 27 define between them a small gap 28 and suitable shaped recesses (not shown) adapted to grip a protruding ball deposit 29 on a substrate 31. U.S. Pat. No. 6,237,422 shows an example of such a recess.

The upper portions 32 of the arms 26 are coupled to respective tension members 22, as illustrated. The tension members may be cylindrical section wires, or may be of flat rectangular section. The joining method is not important, provided it is secure; adhesive or soldering are suitable, but preferably a mechanical hook and/or a mechanical clamp are used. As illustrated mechanical clamps are provided at the outboard ends, and may be tightened when the jaw is in the rest condition.

The mounting limb 24 has three holes 33, two of which are for accurate generally sliding location onto spigot pins, and the third of which is for receiving a retention screw; the screw is typically placed through the centremost hole.

The mass of the jaw is designed to be small, and is further reduced by the use of holes in the arms 26.

A substantial mounting block 34 is secured to the chassis and has mounted thereon a cantilever strain gauge element 35 (FIG. 2) having a central beam 36, and upper and lower arms 37 which have suitable strain gauges mounted thereon. U.S. Pat. No. 6,301,971 discusses the use of strain gauges on members such as arms 37 in test equipment of this type. One type of strain gauge comprises an insulative flexible backing supporting a metallic foil pattern. As the foil is deformed due to stress on the lower arm 37, for example, the electric resistance of the gauge changes. This change in resistance is typically measured using a Wheatstone bridge. The change in resistance can be related to the strain on arm 37 and correlated to the tensile force applied to the solder ball by the jaw 23. Semiconductor strain gauges could also be used.

The jaw 23 is mounted to the free end of the element 35 so that the closing direction thereof is substantially orthogonal to the direction of cantilever extension, and both of these directions are substantially orthogonal to the direction of cantilever bending.

It will be appreciated that shortening of the ram 20 by retracting the shaft into pneumatic cylinder of ram 20 will cause the lower ends of legs 17 to pivot outwardly, applying tension to the members 22, and thus bending the arms 26 about the narrow cross piece 25 to close the jaw gap 28.

The cross piece 25 is comparatively thin to allow bending of the arms 26 without exceeding the yield strength thereof.

Attached to one arm 26 is a flat plate 30 which extends across the other arm 26; this other arm is lightly biased against the plate 30 to allow the jaws to close under friction, and thus with an improved degree of lateral control.

More accurate jaw closing is thus achieved.

Also mounted on the chassis are an air pressure regulator 41 having inlet and outlet connections and a screw adjuster 40, and a pressure gauge 42 (the face of which is not illustrated). The regulator 41, gauge 42 and ram 20 are connected to a source of air under pressure by pipework as illustrated.

Resilience of the jaw 23 determines a natural rest condition of the legs 17. The gap 28 may be adjusted by grub screws 43 acting between the uprights 15 and the legs 17. Such grub screws are arranged to be adjustable independently, and have suitable lock nuts. Alternatively the grub screws may act at the upper ends of the legs 17 and uprights 15.

Also provided between the upper ends of the uprights 15 and adjacent legs 17 are respective coil springs 37. The right spring (as viewed) has relatively fixed ends, but the left screw has one end connected via a screw-threaded adjuster 38. By turning the adjuster, the pre-load applied to one arm of the jaws 23 may be altered, adjusting the closed position. Alternatively the left spring may be adjustable and the right spring non-adjustable; in this case the adjuster is hidden within the cover, when closed.

The flange 21 has a guard 44 provided thereon, and adapted to swing down from the rest position (illustrated) to an active position below the jaw 23. The guard is preferably arranged to move automatically to the rest position when the cartridge is properly attached to a test machine, but otherwise to be in the active position so as to protect the jaw from contact damage.

FIG. 6 illustrates a front elevation of the cartridge 10 with lid 12 in the closed condition. Easy access to the pressure regulator 41 is provided, and the gauge 42 is visible through an aperture of the lid.

Typical dimensions of the cartridge 10 are 240 mm×160 mm×60 mm, and the jaw 23 is about 33 mm high and about 20 mm wide.

The thickness of the jaw is typically about 1 mm, and the jaw is preferably formed by photo-etching from 1 mm stainless steel gauge plate. The mass of the jaw is around 1.5 g.

The cartridge beam 35 is preferably of aluminum, and has a mass of around 2.2 g.

Typical air pressure is around 1 bar to achieve a gripping force at the jaw of around 4.5 kg, depending on jaw geometry, solder ball shape, etc.

The jaw may include tip attachments 45 (FIG. 8) of different material and or section. This permits the jaw to be optimized for wear, and allows machining of suitably spaced jaw cavities. Inserts may be of tool or stainless steel, or may be of carbide if a very fine finish of the cavity is required.

FIGS. 3-5 and 7 illustrate an alternative jaw 51 of much smaller size than jaw 23, but mountable in a cartridge 50 of standard shape and size. It will be understood that the applied gripping force is reduced, commensurate with the lower bonding force, and that the air ram may be sized accordingly.

Figure 5:
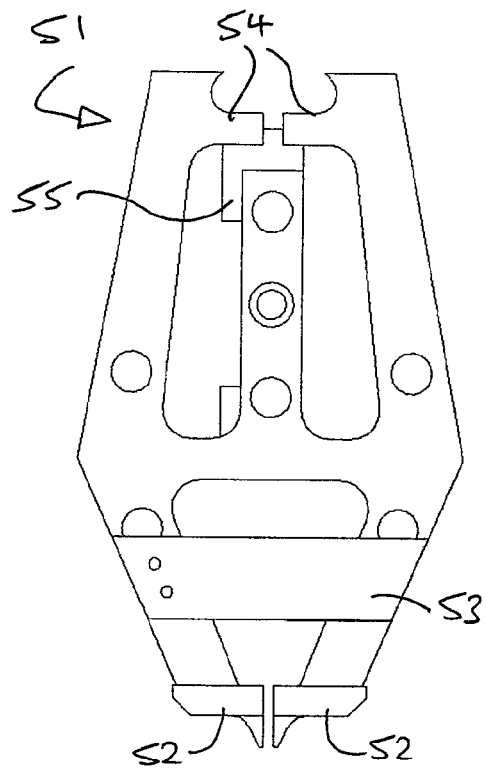
FIG. 5 is an enlarged front elevation of the jaw of FIG. 3.
Figure 4:
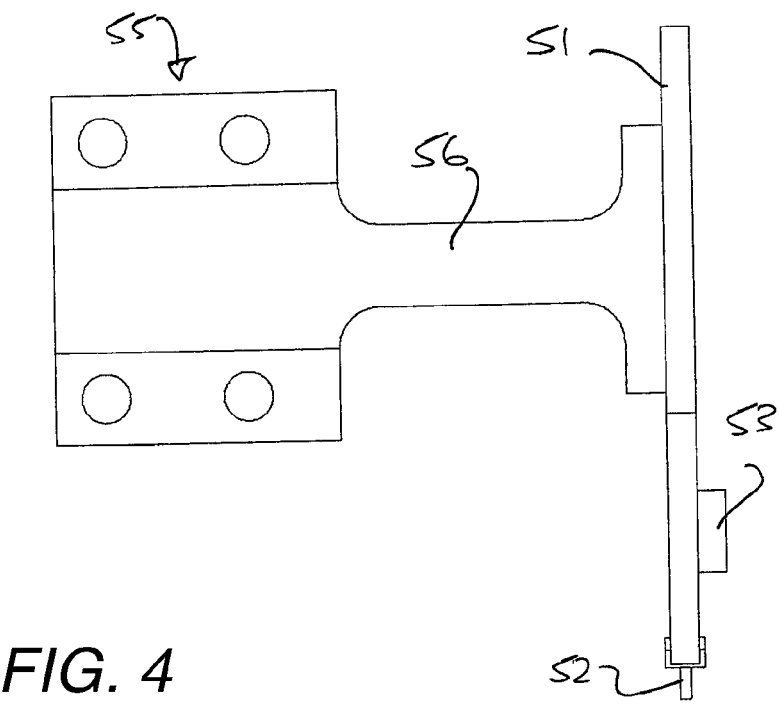
FIG. 4 is an enlarged side elevation of the jaw of FIG. 3 showing the attached cantilever beam.

FIG. 5 shows that the jaw is somewhat simplified, and being smaller does not require apertures to reduce the mass thereof. The 'H' section is common, along with removable tip attachments 52 and a control plate 53. Opposite inwardly facing extensions 54 at the side opposite the attachments 52 limit the stroke of the jaw in the opening direction so as to avoid over-stressing thereof.

Figure 3:
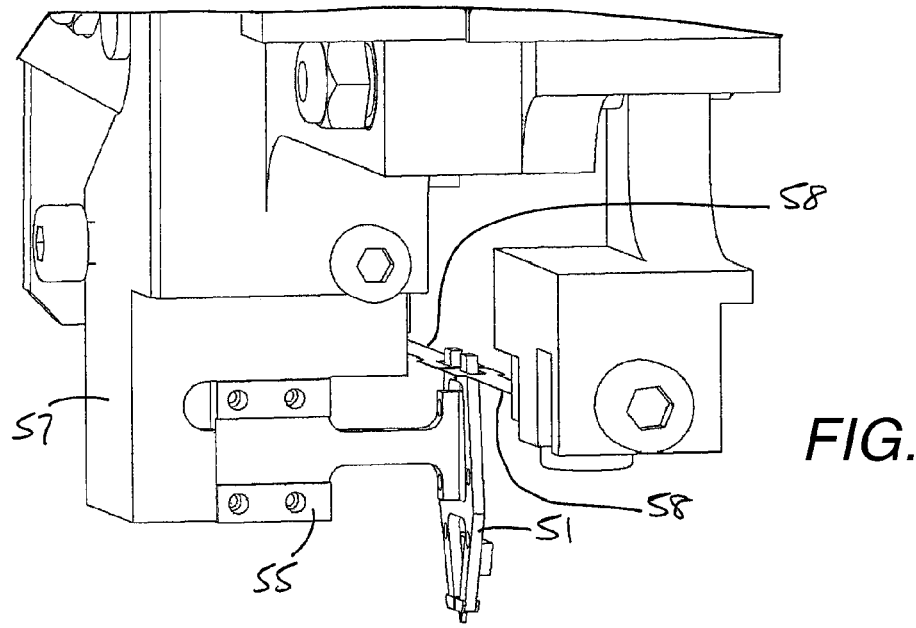
FIG. 3 is an enlarged elevation from one side of an alternative jaw arrangement.

The strain gauge element 55, to which the jaw 51 is mounted, comprises a single cantilever arm 56 which is suitably strain gauged to indicate pulling forces exerted by the jaw. FIG. 3 illustrates the element 55 attached to a mounting block 57 of the chassis. The range of movement in use is small, so that the pulling load is substantially vertical in use.

FIG. 3 also illustrates that the tension members 58 may be flat and plate-like.

Figure 7:
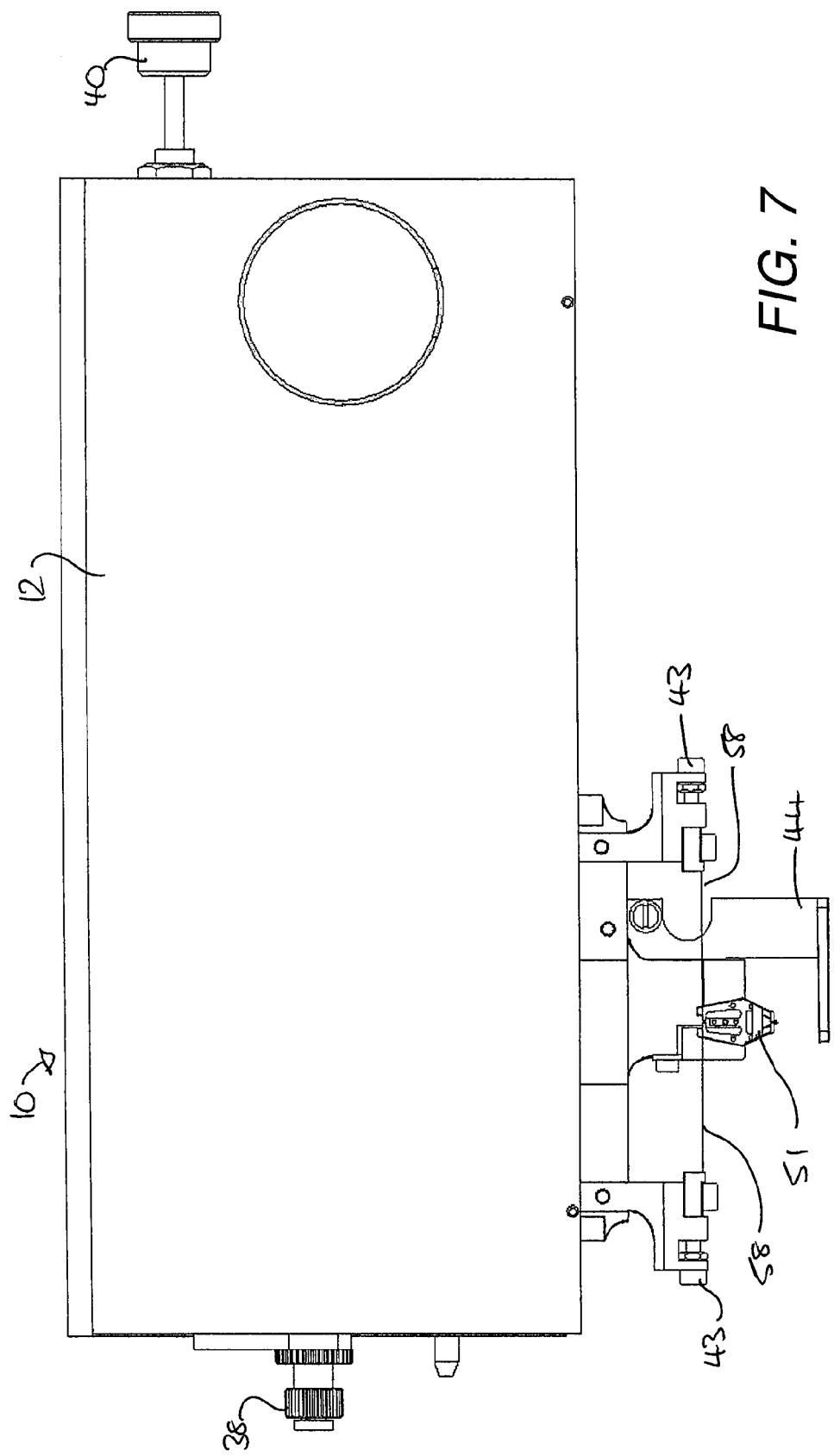
FIG. 7 is a front elevation of a cartridge corresponding to FIG. 3, with cover closed.

FIG. 7 illustrates the guard 44 in the deployed condition, in which the jaw is protected from accidental contact damage.

Use of the apparatus in performing a tensile test is as follows, with additional reference to FIG. 9.

A typical tensile test machine 60 comprises a frame 61 having thereon a platen 62 to which a test sample 63 is securely attached by suitable clamps (not shown). The platen 62 is movable in the X and Y directions (left to right as viewed, and in and out of the drawing plane as viewed) under the control of suitable electric motors. A precision positioning system appropriate to a conventional vertical axis milling machine is suitable.

The frame 61 extends over the platen 62 and includes a head 68 movable in the Z direction (up and down as viewed) under control of a suitable precision electric motor. Mounted securely on the head is a test cartridge 10. As noted above, the act of mounting the head causes a guard 44 to swing up to expose the jaw 23, 51.

The strain gauged element 35, 55 to which the jaw 23, 51 is mounted has an electrical output recorded on a suitable apparatus, typically a personal computer 64, and may give a direct visual output via a screen 65 in addition to recording time, displacement and force characteristic for subsequent analysis.

In use the X-Y table is driven to position a chosen solder ball immediately below the open jaw 23, 51. A suitable vision system may be used, but more preferably an automatic alignment system which may for example be actuated according to a stimulus on the sample, or according to information about the size and spacing of an array of test specimens.

Once vertically aligned, the test cartridge is driven down with jaw open to a predetermined spacing above the substrate of the sample on which the solder balls are formed. At this stage the strain gauge element is unstressed.

The jaw 23, 51 is closed about the solder ball by actuation of the ram 20 and without further movement of the test cartridge 10. The cross piece of the jaw is substantially unaffected by such clamping motion notwithstanding the high clamping force (e.g. 5 kgf) which is imposed. At this stage the strain gauge element remains unstressed and essentially decoupled from the clamping force.

The tensile test is performed on the sample by vertical upward movement of the test cartridge. Upward movement causes the strain gauged element 35, 55 to bend and emit an electrical signal proportional to the force imposed. Eventually the bond between the ball deposit and substrate will break, and allow a breaking force to be calculated from the output of the strain gauge(s).

The very low comparative mass of the jaw is de-coupled from the mass of the ram 20 and associated actuation elements, so that the measured force is more closely representative of the actual forces in the bonding plane.

The apparatus of FIG. 9 may be modified to perform an impact test whereby the tensile test is performed at high speed (at a high rate of increase of strain). Such a test may comprise rapid upward movement of the test cartridge, and platen, and sudden stopping of the platen, as described in International publication WO/2005/093436, the contents of which are incorporated herein by reference.

The speed of testing is selected to simulate the impact forces which may be experienced by equipment to which is fitted electrical components equivalent to the test sample. Such speeds may for example simulate the impact force of a mobile phone when dropped upon the ground, and are to some extent influenced by the mounting arrangements for electrical components within equipment, and any shock absorbing properties thereof. Suitable testing speeds are selectable in a range from virtually zero up to 1000 mm/s. During the test described above the jaw is clamped to the sample and is effectively part of the mass thereof.

By minimizing the mass of the jaw to the greatest extent, and isolating the jaw from the jaw closing apparatus, the inertial effect of the jaw, which in practice tends to increase resistance to movement, is minimized. The apparatus of the invention thus provides for tensile testing which more closely simulates actual failure modes.

A unitary jaw is particularly advantageous because a pivot axis (as in scissors) is not provided, and thus there is no play, friction or lost motion. Furthermore the risk of seizure is eliminated. Yet another advantage is that a unitary jaw is inherently resilient and thus requires no return spring—simplicity and low mass can be assured. Finally, a unitary jaw has a fixed rest condition when unstressed, and thus no setting or backstops are required to maintain a predetermined jaw opening. These are advantages which are realized for all testing speeds.

It is intended to be understood that this invention is not limited to the embodiments described herein and that variants, obvious to those skilled in the art, can be made which are within the spirit of the invention and scope of the apparatus and method claims appended hereto. For example, the jaw of the invention is illustrated in a vertical orientation, pulling upwardly, but other pulling orientations are possible.

The invention claimed is:

1. A tensile test machine comprising:
   a jaw for gripping a deposit on a substrate,
   a frame,
   a movable head mounted to said frame,
   a test cartridge connected to said movable head, and
   pivoting legs attached to said test cartridge, said pivoting legs having a first position and a second position and being connected to said jaw to close said jaw when moved from said first position to said second position,
   wherein said jaw when closed can grip the deposit and wherein said jaw while gripping the deposit can pull the deposit off the substrate when said test cartridge is moved by said movable head.

2. A machine according to claim 1, wherein said jaw is attached to a beam and further including a platen for mounting of a substrate having the deposit to be gripped in use by said jaw, said beam being movable relatively in a first direction towards and away from said platen to position said jaw for gripping.

3. A machine according to claim 2, wherein said platen is relatively movable in a plane perpendicular to said first direction to position said jaw over the deposit to be tested.

4. A machine according to claim 3, wherein said platen is relatively movable in said plane, and said beam is relatively movable on said frame in said first direction.

5. A machine according to claim 1, wherein said jaw is attached to a beam which is supported on said frame, and force measurement elements are provided on said beam.

6. The machine according to claim 5, wherein said jaw includes two rigid members and a central member connecting said two rigid members, each of said rigid members having a first end and oppositely disposed second end, said first ends of said rigid members being attached by tension members to said pivoting legs, said pivoting legs adapted to apply a tension force to said tension members to pull said first ends of said rigid members away from one another, said movement of said first ends away from one another causing said second ends to move towards one another to grip said deposit.

7. A machine according to claim 1, wherein said legs are pivoted by an actuator.

8. A machine according to claim 7, wherein said actuator is a pneumatic cylinder.

9. A machine according to claim 7, wherein respective first ends of said legs are connected to said actuator.

10. A machine according to claim 9, wherein respective second ends of said legs are connected by tension members to said jaw.

11. A machine according to claim 1, wherein said jaw is mounted to a mounting block that include a strain gauge element for measuring the force required to pull the deposit off of the substrate.

12. A jaw of a tensile test device, said jaw comprising a unitary substantially 'H' shaped member having a cross piece adapted for mounting to a strain gauged cantilever beam, and two uprights each having an upper end and a lower end, the upper ends of the uprights being adapted to be urged resiliently apart so as to bring the lower ends of the uprights towards one another to grip a test sample in use; and tension elements attached to said uprights for moving said uprights relative to each other;

wherein said tension elements are adapted to be rigid in tension and compliant in bending so as to resist transmission of non-tensile forces therethrough.

* * * * *

UNITED STATES PATENT AND TRADEMARK OFFICE
CERTIFICATE OF CORRECTION

PATENT NO. : 8,646,337 B2  
APPLICATION NO. : 13/326737  
DATED : February 11, 2014  
INVENTOR(S) : Robert John Sykes Page 1 of 1

It is certified that error appears in the above-identified patent and that said Letters Patent is hereby corrected as shown below:

Title Page:

Item (63), change "filed as application No. PCT/GB2007/002474 on Jul. 3, 2007, now Pat. No. 8,100,021" to --filed December 4, 2008 (now U.S. Patent No. 8,100,021) which is a U.S. National Phase of PCT Application Serial No. PCT/GB2007/002474, filed July 3, 2007 (expired)--.

In the Claims:

Column 9

Claim 11, line 11, change "include" to --includes--.

Signed and Sealed this  
Twentieth Day of May, 2014

Michelle K. Lee  
*Deputy Director of the United States Patent and Trademark Office*